United States Patent [19]

Kozikowski

[11] Patent Number: 5,104,880

[45] Date of Patent: Apr. 14, 1992

[54] HUPERZINE A ANALOGS AS ACETYLCHOLINESTERASE INHIBITORS

[75] Inventor: Alan P. Kozikowski, Ponte Vedre Beach, Fla.

[73] Assignee: Mayo Foundation for Medical Education and Research, Rochester, Minn.

[21] Appl. No.: 694,121

[22] Filed: May 1, 1991

[51] Int. Cl.$^5$ ............... A61K 31/435; C07D 221/22
[52] U.S. Cl. ............................... 514/295; 546/15; 546/97; 546/134; 546/249
[58] Field of Search ............... 546/97; 514/295

[56] References Cited

U.S. PATENT DOCUMENTS 4,929,731  5/1990  Kozikowski ............... 546/97

OTHER PUBLICATIONS

R. J. Wurtman, *Scientific Amer.*, 62 (1988).
J. S. Liu et al., *Can. J. Chem.*, 64, 837 (1986).
W. A. Ayer et al., *Can. J. Chem.*, 67, 1077, 1538 (1989).
Y. E. Wang et al., *Acta Pharmacol. Sinica*, 7, 110 (1986).
G. P. Vincent et al., *Neurosci. Abst.*, 13, 884 (1987).
X. C. Tang et al., *J. Neurosci. Res.*, 24, 276 (1989).
Y. S. Cheng et al., *New Drugs and Clinical Remedies*, 5, 197 (1986).
Y. Xia et al., *J. Amer. Chem. Soc.*, 111, 4116 (1989).
Y. Xia et al., *Tett. Letters*, 30, 3291 (1989).
A. P. Kozikowski, *J. Heterocyclic Chem.*, 27, 97 (1990).
J. R. Atack et al., *J. Pharmacol. and Exper. Ther.*, 249, 194 (1989).
Kozikowski et al., J.A.C.S. 111, 4116 (1989).
Kozikowski et al., J. Chem. Soc. Perkins Trans. I, 195 (1990).
S. Yamada et al., *Tett. Letters*, 2343 (1973).
A. Dornow et al., *Chem. Ber.* 99, 244 (1966).
K. Schreiber et al., *Chem. Ber.* 93, 1848 (1900).
Tang et al., *CA* 106-12878n (1987).
Liu et al., *Chem Abst.* 107-115821p (1987).
Chen et al., *Chem Abst.* 108-143270x (1988).

*Primary Examiner*—Cecilia Shen
*Attorney, Agent, or Firm*—Merchant, Gould, Smith, Edell, Welter & Schmidt

[57] ABSTRACT

An acetylcholinesterase inhibitor is provided of the general formula (I):

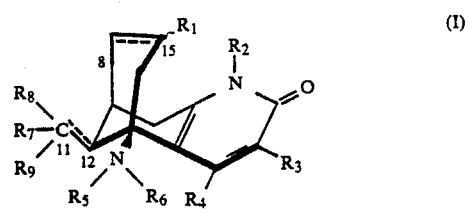

wherein $R_1$ is H, $(C_1-C_8)$alkyl or halo; $R_2$ is H or $(C_1-C_8)$alkyl; $R_3$ and $R_4$ are individually H, $(C_1-C_8)$alkyl, $NO_2$, hydroxy or halo; $R_5$ and $R_6$ are individually H, $(C_1-C_8)$akyl, aryl or aralkyl; $R_7$ is H, halo or $(C_1-C_8)$alkyl, $R_8$ is halo or $(C_1-C_8)$alkyl; $R_9$ is absent or is H; and the bonds represented by—are individually absent or, together with the adjacent bond, form the unit C═C, with the proviso that if both of the bonds represented by—are present, $R_3$ and $R_4$ cannot both be H unless $R_7$ or $R_8$ is halo; and the pharmaceutically acceptable salts thereof.

19 Claims, 3 Drawing Sheets

HUPERZINE A ANALOGS AS ACETYLCHOLINESTERASE INHIBITORS

BACKGROUND OF THE INVENTION

This invention was made with the assistance of National Institute on Aging grant number AGO7591. The Government has certain rights in this invention.

Alzheimer's disease (AD) affects approximately 5-15% of the population of the U.S. over age 65 (1.2-4 million). This disease is frequently associated with individuals over the age of 60 and is the most frequent cause of institutionalization for long-term care. In 1983, more than $27 billion was spent in the U.S. in health care for Alzheimer's afflicted individuals.

Six basic areas of investigation have been defined by R. J. Wurtman, *Scientific Amer.*, 62, (1988), as underlying most research on the causes of Alzheimer's disease. These areas include faulty genes, accumulations of amyloid protein, infectious agents, environmental toxins (e.g., aluminum and certain unusual amino acids), inadequate blood flow and energy metabolism, and lastly cholinergic deficits.

A number of possible therapeutic interventions are currently under study. These include the use of nerve growth factors (NGF), muscarinic and nicotinic agonists, acetylcholinesterase (AChE) inhibitors, GABA-inverse agonists, NMDA modulators, and others. It is, however, unlikely that any single drug will restore cognition, especially in view of the involvement of a number of different neurotransmitter systems in memory processing, and the fact that dead neurons cannot be revived.

To the extent that AChE inhibitors ran serve as useful adjuncts in the treatment of AD, two relatively new lycopodium alkaloids, huperzine A and B, isolated from *Huperzia serrata* (Thunb.) Trev., a Chinese folk medicine, appear superior to THA and physostigmine. J. S. Liu et al., *Can. J. Chem.*, 64, 837 (1986); W. A. Ayer et al., ibid., 67, 1077 (1989), ibid., 67, 1538 (1989). In studies performed in China, these compounds have been found to improve memory and learning in animals. X. C. Tang et al., *Acta Pharmacol. Sinica*, 7, 507 (1986). Additionally, huperzine A has been studied by workers at Hoffmann LaRoche in mice and squirrel monkeys, and the compound has been found to be an effective cognition enhancer. G. P. Vincent et al., *Neurosci. Abst.*, 13, 884 (1987). The duration of action of a single dose (2 mg/kg i.m.) of huperzine A is over 6 hr, a remarkable result in relation to the AChE inhibitory action of physostigmine (0.65 mg/kg i.m.), which has a maximal duration of action of 60 min and which causes considerable side effects. X. C. Tang et al., *J. Neurosci. Res.*, 24, 276 (1989). Huperzine A has further been tested in 128 patients suffering from myasthenia gravis and found to control the clinical manifestations of the disease in 99% of these cases. Y.-S. Cheng, *New Drugs and Clinical Remedies*, 5, 197 (1986).

Analogs of huperzine A have been reported. For example, A. P. Kozikowski et al. (U.S. Pat. No. 4,929,731) disclose the analog of huperzine A, wherein the amino group has been replaced by —$CH_2NH_2$. However, this analog was about 166 times less potent than (±)-huperzine A as an inhibiter of AChE. Therefore, a continuing need exists for analogs of huperzine which exhibit improved potency, high metabolic stability, better partitioning into the brain, and/or a longer duration of action.

SUMMARY OF THE INVENTION

The present invention provides a number of compounds of general formula (I), which are formally derivatives of huperzine A:

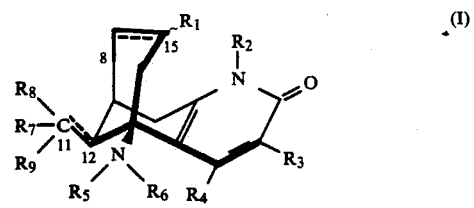

wherein $R_1$ is H, ($C_1$-$C_8$)alkyl or halo; $R_2$ is H or ($C_1$-$C_8$)alkyl; $R_3$ and $R_4$ are individually H, ($C_1$-$C_8$)alkyl, $NO_2$, hydroxy or halo; $R_5$ and $R_6$ are individually H, ($C_1$-$C_8$)alkyl, aryl or aralkyl; $R_7$ is H, halo or ($C_1$-$C_8$)alkyl, $R_8$ is halo or ($C_1$-$C_8$)alkyl, $R_9$ is absent or is H; and the bonds represented by—are individually absent or, together with the adjacent bond, form the unit C=C, with the proviso that if both of the bonds represented by—are present, $R_3$ and $R_4$ cannot both be H unless $R_7$ or $R_8$ is halo; and the pharmaceutically acceptable salts thereof.

Therefore, the genus of compounds of formula I does not include huperzine A itself, or the simple N-alkylated derivatives thereof. Preferably, $R_1$ is H, halo (Cl, Br, I or F, most preferably F) or methyl. Preferably, $R_2$ is H, preferably $R_3$ is nitro or halo, preferably $R_4$ is ($C_1$-$C_4$)alkyl or OH, and preferably $R_5$=$R_6$=H. Preferably $R_7$ and $R_9$ are H and $R_8$ is ($C_1$-$C_4$)alkyl. Preferably, at least one of the bonds represented by—is absent. Therefore, the preferred compounds of formula I are dihydro or bis(di-hydro)analogs of huperzine A which can also comprise substituents on the pyridone ring, or are pyridone ring-substituted analogs of huperzine A.

The compounds of the general formula I or II may exist in the form of optical isomers, and these isomers, as well as racemic (±) mixtures are included within the invention. The present invention also includes both the 12R and 12S, and both the 15R and 15S enantiomers of the present compounds, as well as unresolved or partially resolved mixtures thereof. The term "alkyl" includes linear or branched alkyl. The terms "aryl" and "aralkyl" are fully defined hereinbelow. Preferred aryl groups include phenyl, tolyl, xylyl, anisyl and the like. Preferred aralkyl groups include arlyoxy- and aryl-($C_1$-$C_3$)alkyl moieties.

The $C_{15}$—$R_1$ bond is waved to indicate that the $R_1$ substituent, when present may be equatorial or axial, or a mixture thereof. Although for convenience, the $C_{11}$-$C_{12}$ bond is positioned equatorially, it may be either equatorial, axial or a mixture thereof. The structures of some preferred embodiments of the invention are summarized in Table I, below, along with their bioactivity.

TABLE I

| Compound No. | $R_1$ | $R_2$ | $R_3$ | $R_4$ | $R_5$=$R_6$=$R_7$ | $R_9$ | $R_8$ | $C_8$-$C_{15}$ Dbl Bond[1] | $C_{11}$-$C_{12}$ Dbl Bond[1] | AChE $IC_{50}(M)$[e] |
|---|---|---|---|---|---|---|---|---|---|---|
| Natural | | | | | | | | | | |

TABLE I-continued

| Compound No. | $R_1$ | $R_2$ | $R_3$ | $R_4$ | $R_5=R_6=R_7$ | $R_9$ | $R_8$ | $C_8-C_{15}$ Dbl Bond[1] | $C_{11}-C_{12}$ Dbl Bond[1] | AChE $IC_{50}(M)$* |
|---|---|---|---|---|---|---|---|---|---|---|
| (−)-Huperzine A (1a) or | $CH_3$ | H | H | H | H | — | $CH_3$ | + | + | $0.47 \times 10^{-7}$ |
| (±)-Huperzine A (1) | | | | | | | | | | $0.73 \times 10^{-7}$ |
| 2e (eq. $C_{15}$-Me)[2] | $CH_3$ | H | H | H | H | — | $CH_3$ | − | + | $4 \times 10^{-6}$ |
| 2a (ax. $C_{15}$-Me)[3] | $CH_3$ | H | H | H | H | — | $CH_3$ | − | + | $1 \times 10^{-6}$ |
| 3 | H | H | H | H | H | — | $CH_3$ | − | + | $1.3 \times 10^{-5}$ |
| 4 | $CH_3$ | H | H | $CH_3$ | H | — | $CH_3$ | + | + | N/T |
| 5 | $CH_3$ | H | H | OH | H | — | $CH_3$ | + | + | N/T |
| 6 | $CH_3$ | H | $NO_2$ | H | H | — | $CH_3$ | + | + | N/T |
| 7 | $CH_3$ | H | Cl | H | H | — | $CH_3$ | + | + | N/T |
| 8 (ax. $C_{12}$—Pr) | $CH_3$ | H | H | H | H | H | Et | + | − | N/T |
| 9 (eq $C_{12}$—Pr) | $CH_3$ | H | H | H | H | H | Et | + | − | N/T |
| 10 | Et | H | H | H | H | — | $CH_3$ | + | + | N/T |
| 11 | F | H | H | H | H | — | $CH_3$ | + | + | N/T |
| 12 | H | H | H | H | H | — | $CH_3$ | + | + | N/T |
| 13 | $CH_3$ | H | H | H | H | — | Cl | + | + | $8.09 \times 10^{-7}$ |

*Assayed using rat hippocampal crude homogenates over a concentration range of $10^{-11}$M to $10^{-3}$M. These compounds were all dissolved in 10% DMSO made up in the incubation buffer medium. In addition, those substances which did not dissolve readily were treated with mild hydrochloric acid and sonicated briefly until they dissolved in the solution. In each case, the control medium always consisted of the same ingredients as those which were used to dissolve the compound under investigation. AChE was measured as described in Example 4.
[1](+) = $C_8-C_{15}$ or $C_{11}-C_{12}$ double bond is present; (−) = $C_8-C_{15}$ or $C_{11}-C_{12}$ double bond is absent.
[2]C-15 methyl is R-configuration.
[3]C-15 methyl is S-configuration.

The compounds of formula I, or mixtures thereof, are useful as inhibitors of acetylcholinesterase (AChE), and thus may be useful in clinical settings, for the treatment of memory and learning disorders. Such conditions include Alzheimer's dementia (AD), myasthenia gravis, and other age-related memory impairments. While it is known that defects in neurotransmitter systems other than cholinergic system play a role in the memory loss associated with AD, findings by K. L. Davis, presented at "New Strategies for the Treatment of Alzheimer's Disease," NIA meeting (Jan. 8–10, 1990) indicate that AChE inhibitors, such as physostigmine, do show modest cognitive improvement, and may prove useful in combination with other drugs, e.g., clonidine, deprenyl or desipramine. Specifically, the use of at least one compound of formula I, in combination with an efficacious M2 antagonist which facilitates acetyl choline release, may constitute an effective therapeutic strategy.

All percentages given herein are by weight unless otherwise noted.

DETAILED DESCRIPTION OF THE INVENTION

Huperzine A and Intermediates in the Synthesis Thereof

Figure 1:
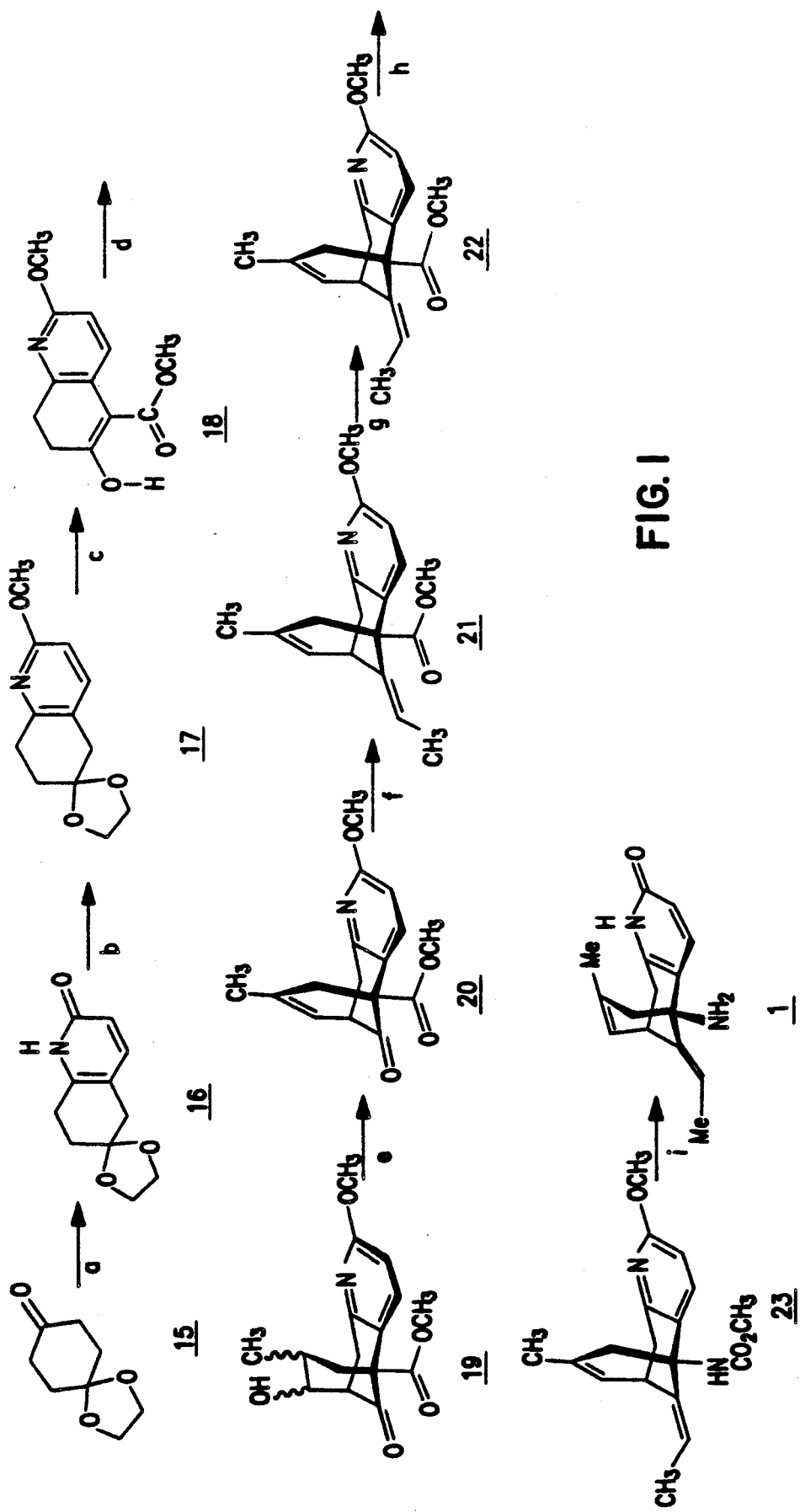
FIG. 1 is a schematic depiction of the synthesis of huperzine A (1).

The synthesis of huperzine A (1) can be accomplished as shown in FIG. 1 from 1,4-cyclohexanedione (15) as disclosed by A. P. Kozikowski et al., *J. Amer. Chem. Soc.*, 111, 4116 (1989) and A. P. Kozikowski et al., *J. Chem. Soc., Perkins Trans. I*, 195 (1990). The reagents and reaction conditions used to accomplish steps a–i are summarized in Table II, below.

TABLE II

| Step | Synthesis of Huperzine A Reaction Conditions | Yield |
|---|---|---|
| a | $NH_3$, $MeO_2CC\equiv CH$, 150° C., 10 hr, 300–350 psi | 70% |

TABLE II-continued

| Step | Synthesis of Huperzine A Reaction Conditions | Yield |
|---|---|---|
| b | $Ag_2CO_3$, MeI, $CHCl_3$, reflux, 2 hr | 92% |
| c | 5% HCl, acetone (1:1), reflux, 3 hr; | 85% |
| | then KH, $(MeO)_2CO$, reflux, 3 hr | 87% |
| d | methacrolein, tetramethylguanidine (TMG), $CH_2Cl_2$, 25° C., 4 hr | 93% |
| e | MsCl, $Et_3N$, DMAP, $CH_2Cl_2$; | 96% |
| | then NaOAc, HOAc, 110° C., 24 hr | 50% |
| f | $Ph_3P=CHCH_3$, THF, 0° C. to 25° C. | 73%[1] |
| g | PhSH, AIBN, 170° C., 24 hr | 100%[2] |
| h | 20% NaOH, THF, MeOH, reflux, 48 hr; | 78%[3] |
| | then $SOCl_2$, toluene, 80° C., 2 hr; then | 80% |
| | $NaN_3$, 80° C.; then MeOH, reflux | (overall) |
| i | TMSI, $CHCl_3$, reflux | 92% |

[1]E/Z = 10:90;
[2]E/Z = 90:10;
[3]Based on E-ester.

Dihydrohuperzine A and C-15-Desmethylhuperzine A

Figure 2:
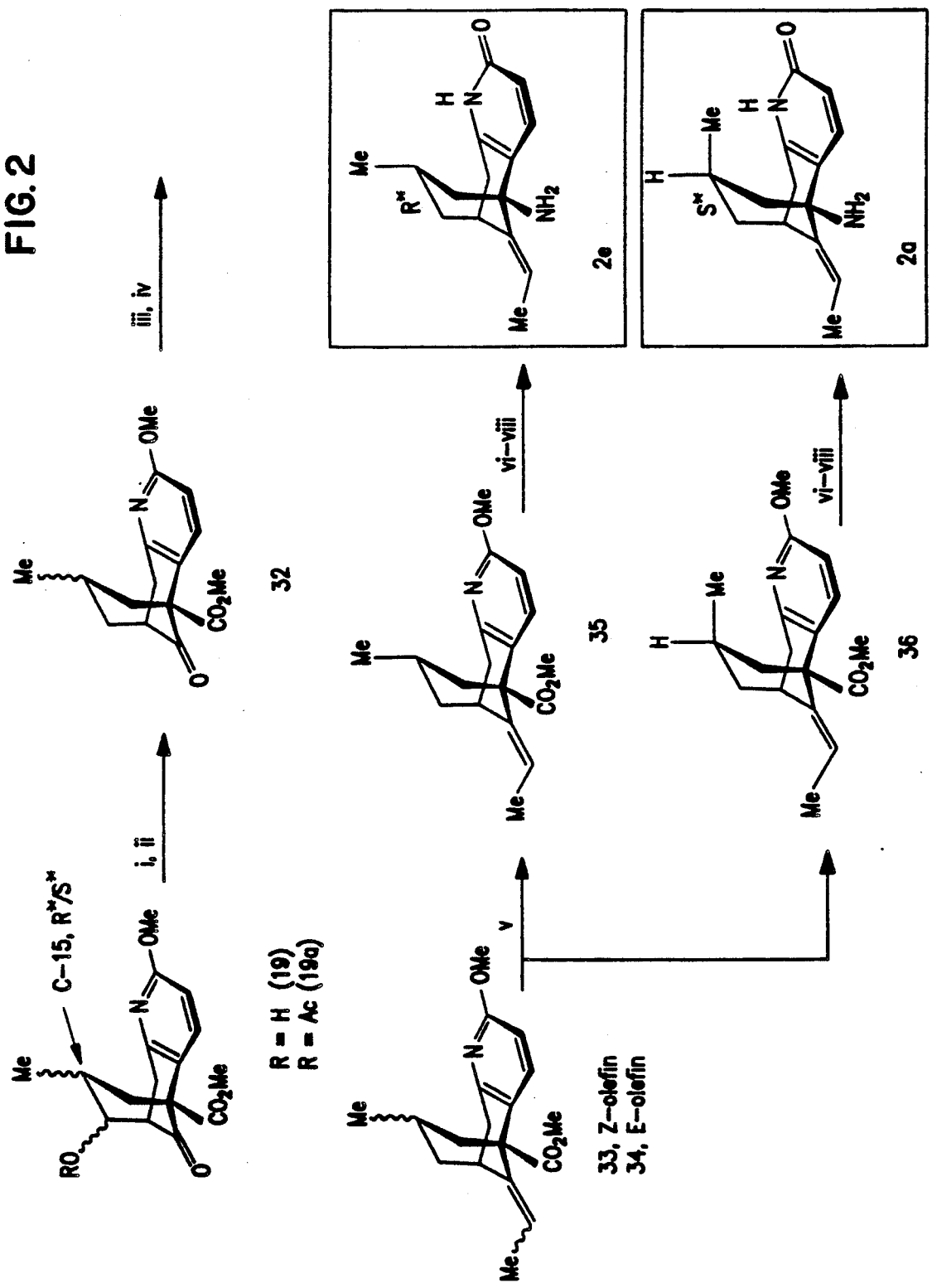
FIG. 2 is a schematic depiction of the synthesis of the 8,15-dihydro analogs of huperzine A.

FIG. 2 summarizes the synthesis of the 8,15-dihydrohuperzine A isomers 2a and 2e from intermediate 19 (see FIG. 1). The reagents and reaction conditions used to accomplish steps i–viii are outlined in Table III, below.

TABLE III

| Step | Synthesis of 8,15-Dihydrohuperzine A Analogs Reaction Conditions | Yield |
|---|---|---|
| i | $(imd)_2C=S$, THF, 70° C., 24 hr | 88% |
| ii | $(n-Bu)_3SnH$, AIBN, PhMe, 125° C., 2.5 hr | 92% |
| iii | $EtPPh_3Br$, KOtBu, THF, 4 hr, 25° C. | 75% |
| iv | PhSH, AIBN, PhMe, 100° C., 24 hr | 93% |
| v | Separate mixture by silica gel chromatography to get pure 35, then resubmit mixture of 36 and 33/34 to conditions of iv to get pure 36 after chromatography | — |
| vi | 20% NaOH, THF, MeOH, 100° C., 24 hr | 70% |
| vii | $(PhO)_2P(O)N_3$, $Et_3N$, PhMe, 90° C., 3 hr; then MeOH, 70° C., 11 hr | 67% |
| viii | TMSI, $CHCl_3$, 65° C., 10 hr; then MeOH, 65° C., 2.5 hr | 68% |

As shown in FIG. 2, the synthesis of both the C-15 R*- and S*-isomers of dihydrohuperzine A was carried out starting from the previously reported β-keto ester 19. The hydroxyl group of 19 was removed by a Barton-type deoxygenation reaction employing 1,1'-thiocarbonyldiimidazole and tri-n-butyltin hydride. (D. H. R. Barton et al., *Chem. Commun.*, 867 (1976)). Next, a Wittig reaction was carried out on 32 employing ethylidenetriphenylphosphorane, and the 1:3 E/Z-mixture initially formed was isomerized to an 8:1 E/Z-mixture of 33/34 by use of AIBN/PhSH. At this juncture, it was possible to separate the E- and Z-isomers, and additionally, to separate the C-15 R*-isomer 35 of E-olefin geometry from the C-15 S*-isomer 36 of E-geometry (for details see FIG. 2 and Table II).

These stereoisomers were converted individually to the corresponding dihydrohuperzine analogs 2a and 2e by base hydrolysis, Curtius rearrangement [(PhO)$_2$P(O)N$_3$] in accord with S. Yamada et al., *Tett. Letters*, 2343 (1973), and deprotection (TMSI). Since NMR proved inadequate for the purpose of assigning the stereochemistry of the C-15 center to these products, an X-ray analysis was carried on one of the crystalline acetate derivatives (19a) of alcohol 19. Subsequent chemical transformations correlated the structure of this crystalline derivative (19a, C-15 R*-stereochemistry) with the equatorial C-15 methyl analog 2a.

Because of the tedious chromatographic separations required to produce these dihydro analogs, the synthesis of C-15 desmethyl-dihydrohuperzine A (3) was carried out. The synthetic route required to produce 3 was identical to that recorded in FIG. 2 with the exception that the C-15 desmethyl analog of 19, available in 84% yield from the reaction of β-keto ester 18 (see FIG. 1) with acrolein in CH$_2$Cl$_2$ with tetramethylguanidine ($-78°$ C., 30 min then warm to 25° C. over 1 hr and 25° C. for 2 hr), was substituted for 19 and step v was omitted.

The activity of these new compounds was assayed using AChE isolated from rat brain. Not surprisingly, compounds 2e and 2a were found to be less active than natural ($-$)-huperzine A. The IC$_{50}$ value for compound 2e is $4 \times 10^{-6}$ M, and that of compound 2a is $10^{-6}$ M compared to an IC$_{50}$ of $0.47 \times 10^{-7}$ M for ($-$)-huperzine A. The unsaturated three-carbon bridge of huperzine A thus contributes to its AChE inhibitory activity, and the slight loss in activity of the dihydro compounds may be attributed to steric and electronic effects together with an entropic factor. The steric interaction existing between the C-15 methyl group of 2a and its pyridone ring forces 2a to adopt a shape more closely resembling that of huperzine A, thus explaining its lower IC$_{50}$ value.

The desmethyl compound 3 exhibited an IC$_{50}$ of $1.3 \pm 0.2 \times 10^{-5}$ M. Considering the racemic nature of compound 3, it is thus at least fifty-fold less potent than natural huperzine A. However, since all three of these analogs may exhibit increased metabolic stability or an enhanced ability to cross the blood-brain barrier, they are candidates for further pharmacological evaluation.

Synthesis of Pyridone Ring-Substituted Analogs of Huperzine A.

Huperzine A analogs comprising a hydroxy or alkyl group at the 3-position or a halo or nitro group at the 2-position (huperzine numbering) can also be prepared. These representative analogs are chosen so as to include substituents exhibiting a range of Hammett σ and Hansch π constants. The substituents will also have an effect on the nature of the interaction between the serine hydroxyl present at the esteratic site and the pyridone ring carbonyl group.

To assemble the hydroxy and methyl compounds, the 1,4-cyclohexanedione monoethyleneketal 15 is simply reacted with acetoacetamide in the presence of PPA (A. Dornow et al., *Chem. Ber.*, 99, 244 (1966)) to give the methyl pyridone 40, or with ammonia and dimethyl malonate (K. Schreiber et al., Chem. Ber., 93, 1848 (1960)) to yield the hydroxy-pyridone 41. Once these starting compounds are in hand, the remaining steps of the synthesis are carried out as in the synthesis shown in FIG. 1, to yield analogs 4 and 5, as shown in Scheme 1.

By directly carrying out chlorination or nitration reactions on huperzine A, in accord with the procedure of C. A. Salemink et al., *Rec. Trav. Chim*, 68, 1013 (1949), the products 6 and 7 of attack at the 3-position of the pyridone ring (i.e., position 2 by the huperzine numbering scheme) result, as shown in Scheme 1. If NHCl formation occurs, an additional reduction step can be carried out.

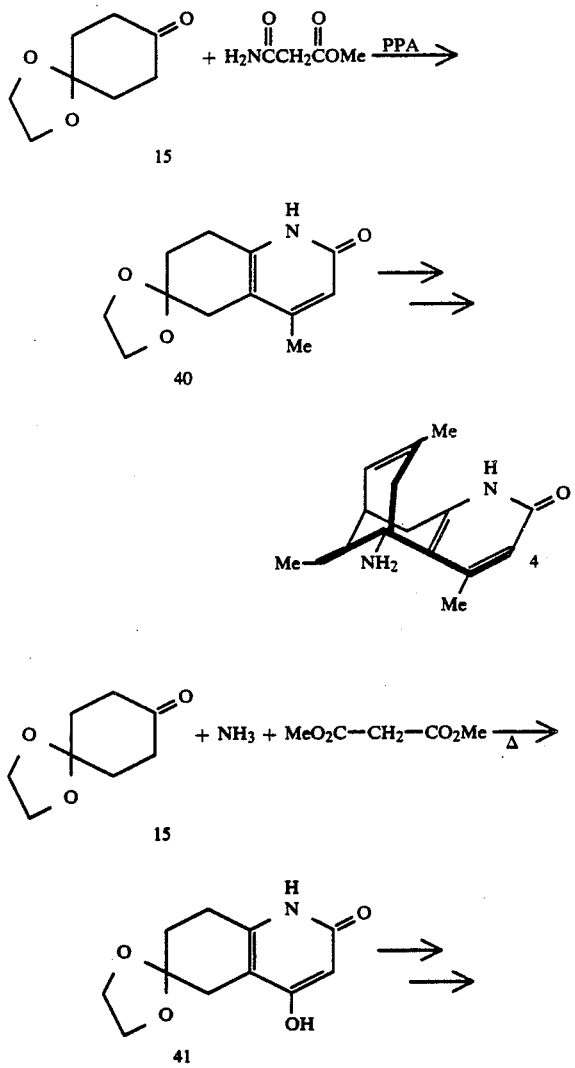

Scheme 1
Pyridone Ring Modified Analogues

-continued
Scheme 1
Pyridone Ring Modified Analogues

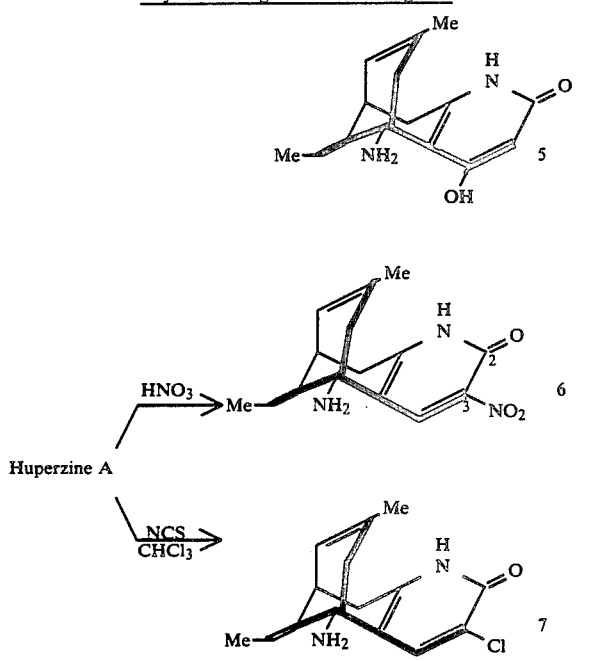

Similarly, iodinated ($^{123}$I) or fluorinated ($^{18}$F) derivatives can be prepared for use in brain imaging by PET. Such compounds would be of value in quantifying regional changes in AChE that take place during the progression of AD. Although AChE is not a specific marker for the disease, it can nonetheless be used to map cholinergic deficits. A los of AChE is prominent in cerebral cortex and hippocampus in patients.

($C_{11}$–$C_{12}$)Dihydrohuperzine A Analogs

Dihydro analogs bearing an alkyl group (ethyl, propyl, etc.) in place of the ethylidene group at $C_{12}$ (huperzine numbering) are prepared by reaction of the ketol 19 with the appropriate Wittig reagent, followed by hydrogenation, and dehydration to yield the tricyclic compound 53, as shown in Scheme 2, wherein R=($C_1$–$C_8$)alkyl. The remaining steps of the synthesis, to yield 8 and 9 when R=$CH_3$, follow the course depicted in FIG. 1. Analog 53 can be synthesized as a mixture, and separated by chromatography, in order to assess the effect of $C_{12}$ stereochemistry on AChE inhibitory activity.

Scheme 2
Alterations at Huperzine's $C_{12}$ Center

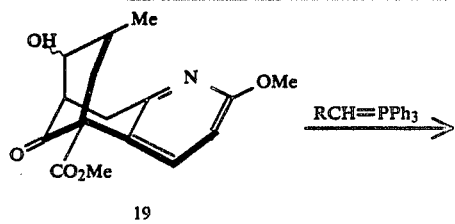

-continued
Scheme 2
Alterations at Huperzine's $C_{12}$ Center

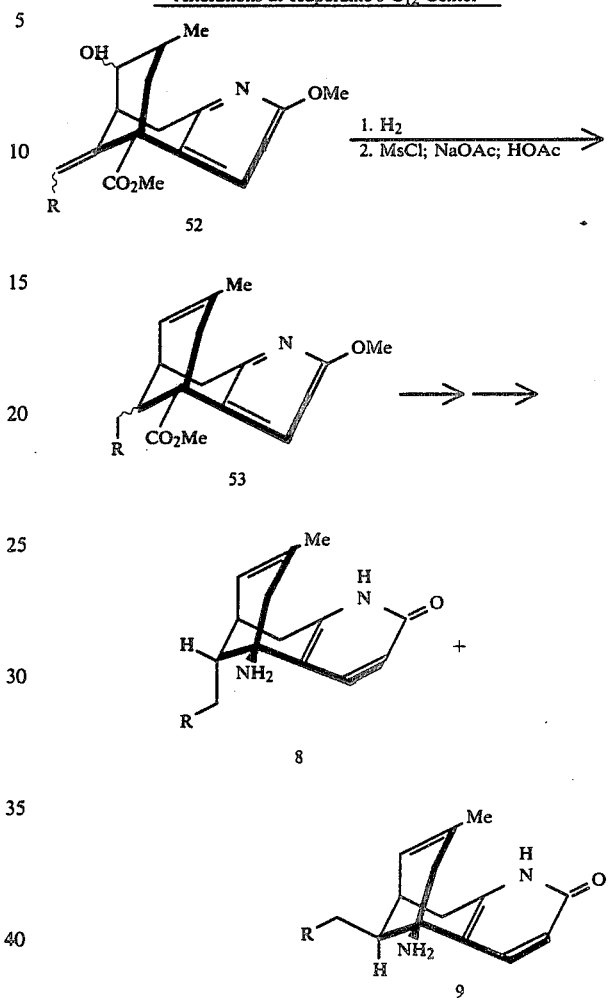

Figure 3:
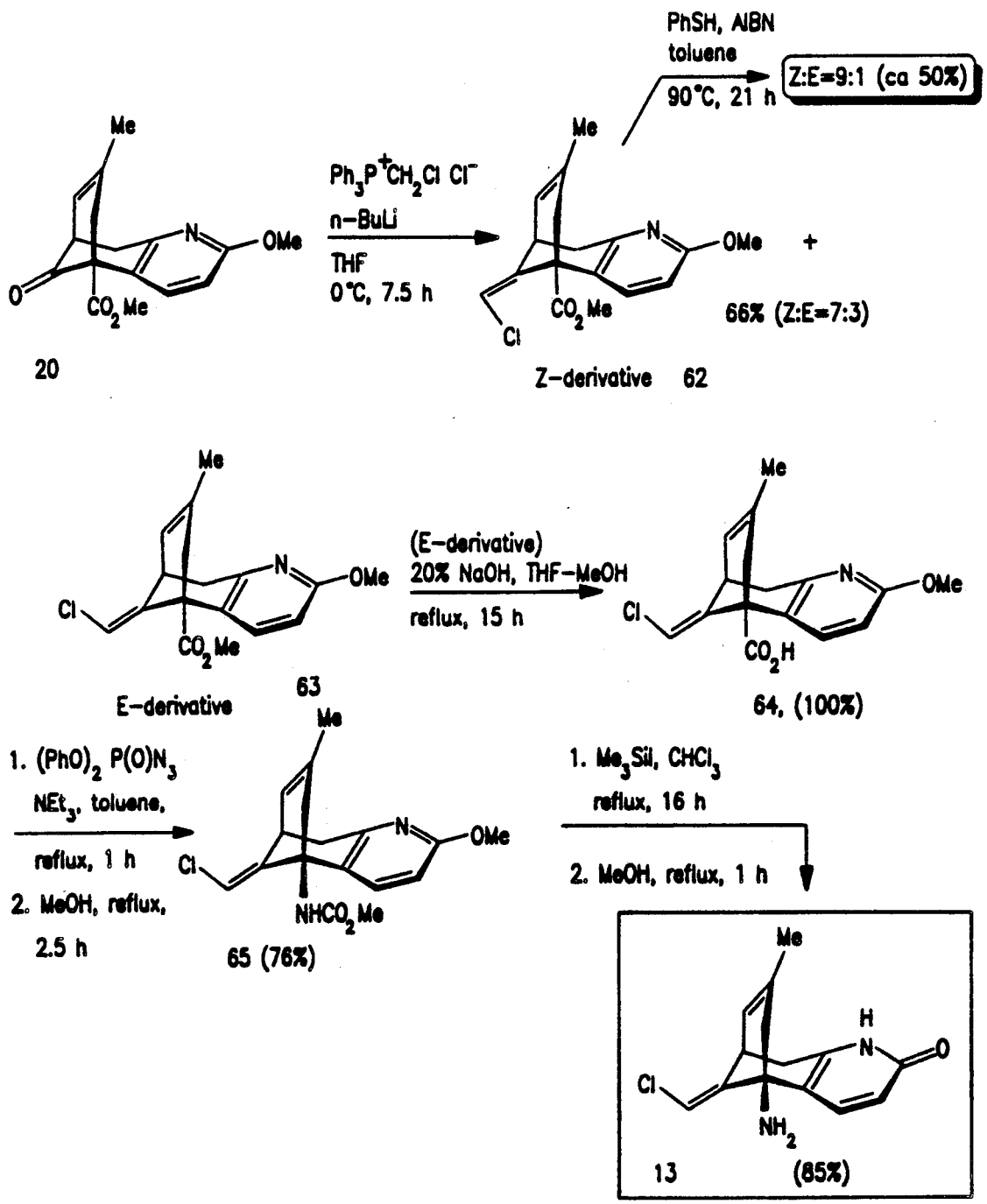
FIG. 3 is a schematic depiction of the synthesis of 11-chloro-huperzine A (13).

Use of Wittig reagents of the general formula ($R_7$)($R_8$)C=$PPh_3$ wherein $R_7$ and $R_8$ are individually ($C_1$–$C_8$)alkyl, will yield various analogs in which $C_{11}$ is bis(alkyl)-substituted. Reaction of Wittig reagents of the general formula ($R_7$)($R_8$)C=$PPh_3$ wherein $R_8$ is halo, and $R_7$ is H with intermediate 20 as shown on FIG. 3, will yield various analogs in which the $C_{11}$ of huperzine is substituted with halo, e.g., analog 13.

C-15-Desmethyl Analogs of Huperzine A

The use of acrolein or α-alkylacroleins such as α-ethylacrolein in place of methacrolein in the Michael-/aldol reaction with compound 18, as shown in Scheme 3, can yield analogs with H or a ($C_2$–$C_8$)alkyl group in place of the C-15 methyl group of huperzine A. The $C_{15}$-methyl group can also be replaced by halo, e.g., by fluoro, by the use of α-fluoroacrolein in place of methacrolein in the same reaction scheme, to yield compound 11.

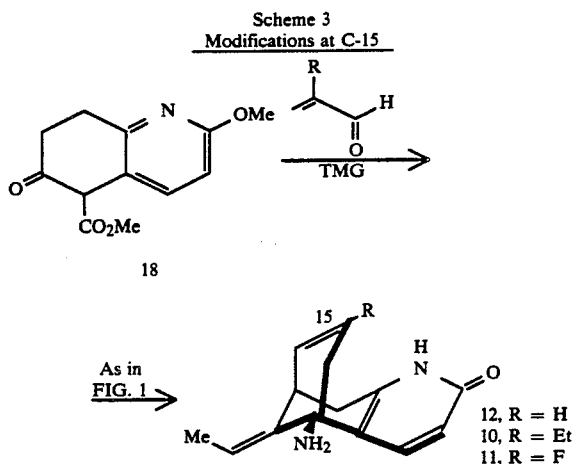

The reaction of huperzine A or the compounds of formula I wherein $R_2=H$ to yield N-alkyl substituted analogs of general formula 50 ($R=(C_1-C_8)$alkyl) can be accomplished as depicted in Scheme 4 for huperzine (benzostabase formation, N-alkylation with alkylhalide RX, and deprotection).

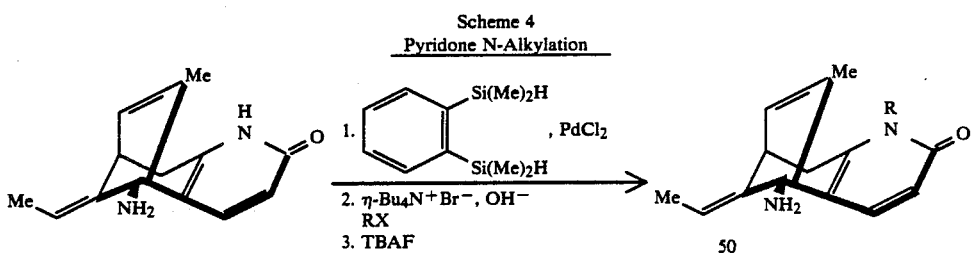

Mono- or disubstituted bridgehead amino compounds of formula I, wherein $R_5$ and $R_6$ are $(C_1-C_8)$alkyl, aryl, aralkyl or mixtures thereof with H, can be prepared by conventional methods for the conversion of primary amino groups to secondary or tertiary amino groups. For example, see I. T. Harrison et al., *Compendium of Organic Synthetic Methods*, Wiley-Interscience, N.Y. (1971) at pages 240–246. Preferred aryl groups include $C_6-C_{10}$ aryl groups substituted with 1–3 $(C_1-C_8)$alkyl, halo, $(C_1-C_4)$, alkoxy and the like, including phenyl, tolyl, xylyl, anisyl, and the like. Preferred aralkyls include those in which said aryl groups are joined to the amino group by a $(C_1-C_8)$ straight-chain or branched alkyl group, in which 1–2 carbons are optionally replaced by —O—, S, or —N—, e.g. aralkyl is preferably $C_7-C_{18}$, wherein the aryl portion is optionally substituted as above.

Pharmaceutically acceptable acid salts of the present compounds can be prepared as described in U.S. Pat. No. 4,383,114.

The compounds of formula I can be employed, singly or in combination, in an amount effective to inhibit the cholinesterase enzymes (such as AChE) in a mammal (such as a human) in need of such treatment. Therefore, the present invention also includes a pharmaceutical composition, such as one or more unit dosage forms, of an effective enzyme-inhibiting amount of one or more of the compounds of formula I in combination with a pharmaceutically acceptable carrier therefor. Such compositions can be administered orally or parenterally, including via intravenous, intramuscular, intraperitoneal, subcutaneous or topical administration.

For oral use of a compound of general formula I, said compound can be administered, for example, in the form of tablets or capsules, or as an aqueous solution or suspension. In the case of tablets for oral use, carriers which are commonly used include lactose, mannitol and corn starch, and lubricating agents, such as magnesium stearate, are commonly added. For oral administration in capsule form, the compound can be administered in dry form in a hard gelatin capsule or in a suitable gelled or liquid vehicle, such as a liquid polyethylene glycol or a carrageenan gel, in a soft gelatin capsule. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparations isotonic.

When a compound according to general formula I is used as in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 1 mg/kg of body weight, and preferably, of from 0.1 mg/kg to about 0.5 mg/kg of body weight, administered in single or divided doses. In some cases, however, it may be necessary to use dosages outside these limits.

The invention will be further described by reference to the following detailed examples, wherein tetrahydrofuran was distilled from sodium benzophenone ketyl prior to use. Toluene was distilled from calcium hydride prior to use. Methylene chloride was dried by passing through a column of activity I neutral alumina and stored over 4 Å molecular sieves. Triethylamine was distilled from calcium hydride and stored over NaOH pellets. Solvents used in chromatography were generally bought in bulk and then distilled in an all-glass apparatus and stored in glass bottles.

Silica gel 60 (Merck, 70–230 (mesh or 230–400 mesh) was used for column chromatography. TLC was performed on Merck silica gel 60 F-254 plates (0.25 mm, precoated on glass). Compounds were analyzed by viewing under a UV lamp or staining with Vaughn's reagent (800 ml of a 10% aqueous sulfuric acid solution, 38g ammonium molybdate, and 1.6 g of ceric sulfate) or a potassium permanganate solution (potassium carbonate (20 g), potassium permanganate (3 g), and 5% sodium hydroxide solution (5 ml) in 300 ml of water).

IR spectra were obtained on a Matteson CYGNUS 100 spectrometer using NaCl plates with the sample either neat or as a thin film as indicated. $^1$H NMR spectra were taken on a Bruker AF-300 (300 MHz) spectrometer in the specified solvents. $^{13}$C NMR spectra were taken on either a Bruker AF-300 (75 MHz) or Bruker AM-500 (125 MHz) spectrometer in CDCl$_3$ or other solvents as indicated. Chemical shifts are reported in parts per million ($\delta$) with reference to CDCl$_3$ (7.26 ppm ($^1$H) or 77.09 ppm ($^{13}$C)). Mass spectra were obtained on a Varian MAT CH 5 or VG 70-G instrument.

EXAMPLE 1

DIHYDROHUPERZINE ANALOGS

A. Deoxygenation Product (32)

A mixture of aldol adduct 19 (3 g, 9.85 mmol) and thiocarbonyldiimidazole (2.1 g, 11.8 mmol) was heated at 70° C. in a sealed tube containing 10 ml of THF. After 20 hr, the reaction mixture was evaporated and the residue column- chromatographed on silica gel (2:3 ethyl acetate/hexanes) to yield 3.6 g (88%) of the ester as a white foam containing four thiocarbonylimidazole isomers: Rf=0.1–0.3 (2:3 ethyl acetate/hexanes); IR (neat) 3130, 2960, 1738, 1730, 1600, 1580, 1460, 1375, 1325, 1290, 1240, 1225, 1118, 1033, 1000, 975, 928, 918, 830, 750, 665 cm$^{-1}$; MS (El) m/e 415 (M+).

A solution of the above product (614 mg, 1.48 mmol), n-Bu$_3$SnH (0.896 ml, 2.22 mmol) in 5 ml toluene was thoroughly purged with argon, and treated with a catalytic amount of azoisobutyric dinitride (AIBN). The solution was heated at 125° C. for 2.5 hr in a sealed tube. The reaction mixture was evaporated and the residue chromatographed on silica gel (hexanes then 1:19 ethyl acetate/hexanes) to give 32 (392 mg, 92%) as an oil containing a 1:1 ratio of the two isomers; IR (neat): 2954, 2872, 1744, 1727, 1601, 1575, 1480, 1461, 1424, 1328, 1266, 1252, 1194, 1181, 1116, 1100, 1086, 1056, 1032, 828 cm$^{-1}$; MS m/e 289 (M+).

B. Ethylidene Compounds (33–36)

(Ethyl)triphenylphoshonium bromide (5.1 g, 13.7 mmol) and potassium t-butoxide (1.38 g, 12.3 mmol) were stirred in 10 ml of THF for 20 minutes. The mixture was cooled to 0° C. and a solution of ketone 32 (1.10 g, 3.81 mmol) in 5 ml of THF was added dropwise. The reaction mixture was allowed to warm to 25° C., stirred for a period of 4 hr, and quenched with a saturated ammonium chloride solution. THF was evaporated and the residue extracted with ethyl acetate and the combined organic extracts dried over sodium sulfate. Filtration, evaporation, and column chromatography on silica gel (hexanes then 2:23, ethyl acetate/hexanes), gave 850 mg (74%) of a mixture containing 33 (Z-isomer) and 34 (E-isomer) in a 3:1 ratio; IR (neat) 2950, 2922, 2869, 1734, 1700, 1653, 1601, 1576, 1560, 1507, 1477, 1465, 1457, 1436, 1425, 1327, 1315, 1265, 1241, 1033 cm$^{-1}$; MS m/e 301 (M+).

A solution containing 33 and 34 (3:1, 1.23 g, 4.1 mmol), thiophenol (1.5 ml, 12.7 mmol), AIBN (0.9 g, 5.49 mmol), and 7.5 ml toluene was purged for 5 minutes with argon and then heated to 100° C. for a period of 24 hr. The solvent was evaporated and the residue chromatographed on silica gel (hexanes then 1:19, ethyl acetate/hexanes) to give 33 and 34 (1.14 g, 93%) in a (1:8) ratio. This mixture was then rechromatographed carefully (3:97, ethyl acetate/hexanes). In this way, it was possible to obtain 35 as the more polar fraction along with a less polar fraction containing a mixture of 33 and 36. In order to get 36, it is necessary to either resubmit the mixture of 36 and 33 to isomerization conditions and once again chromatograph, or the mixture can be carried on to the carbamate stage where the separation is much easier. The Z-carbamate is much less polar. E-equatorial methyl isomer 35; IR (neat) 2949, 2924, 2870, 1729, 1600, 1478, 1324, 1239, 1033 cm$^{-1}$; MS m/e 301 (M+); isomer 36 (axial C$_{15}$-methyl isomer); IR (neat) 2950, 2925, 2883, 2871, 2866, 1730, 1601, 1575, 1478, 1462, 1456, 1424, 1324, 1264, 1239, 1032 cm$^{-1}$; MS m/e 301 (M+).

C. Preparation of Dihydrohuperzines 2a and 2e

A solution containing 35 (250 mg, 0.83 mmol), 0.75 ml THF, 0.75 ml 20% aqueous NaOH solution, and 1.5 ml methanol were heated together at 100° C. in a sealed tube for 24 hr. The organic solvents were then evaporated and the aqueous residue adjusted to pH 7 with a 5% aqueous solution of HCl. The aqueous solution was extracted with methylene chloride, dried over sodium sulfate, filtered, evaporated, and chromatographed on silica gel (1:9, ethyl acetate/hexanes to elute starting material then 1:1 ethyl acetate/hexanes), to yield the corresponding carboxylic acid (135 mg, 57%) as a white foam. Yield based on recovered starting material is 71%; IR (neat) 3500–2300 br., 2928, 2848, 1703, 1599, 1578, 458, 1427, 1298, 1265, 1032, 910, 823, 732 cm$^{-1}$. The corresponding carboxylic acid was prepared from 36 by the same methodology (axial methyl isomer); IR (neat) 3500–2300 br., 2950, 2871, 2589, 1713, 1698, 1599, 1575, 1479, 1423, 1313, 1264, 1033, 821, 737 cm$^{-1}$.

A solution of the carboxylic acid corresponding to 35 (229 mg, 0.80 mmol), triethylamine (0.14 ml, 1.1 mmol), diphenylphosphoryl azide (0.25 ml, 0.98 mmol), and 4 ml of toluene was heated in a sealed tube at 90° C. for 3 hr. The solvent was evaporated and the residue taken up in approximately 5 ml of dry methanol. This mixture was heated at 70° C. for 11 hr. The methanol was evaporated and the residue column-chromatographed on silica gel (1:9 ethyl acetate/methylene chloride) to give the corresponding carbamate (170 mg, 67%) as a white foam; IR (neat) 3500–2300 br., 3300, 2950, 2926, 1721, 1598, 1475, 1311, 1251, 1023 cm$^{-1}$.

The 36-carbamate was prepared by the same methodology: IR (neat): 3500–2300 br., 3330, 2950, 2926, 2869, 1716, 1599, 1527, 1476, 1422, 1315, 1261, 1035 cm$^{-1}$.

Iodotrimethylsilane (0.25 mL, 1.75 mmol) was added dropwise to a solution of the 35-carbamate (25 mg, 0.079 mmol), in 3 ml of dry chloroform. After heating the solution at 65° C. for 10 hr in a sealed tube, the chloroform was evaporated and replaced by 3 ml of methanol and heated at 65° C. for an additional 2.5 hr. The methanol was evaporated and the residue chromatographed (1:19 methanol/chloroform) on silica gel half-saturated with ammonia to give 2e (13 mg, 67%) as a white foam; IR (neat) 3370, 3276, 2922, 2869, 1657, 1616, 1554, 1458, 832, 731 cm$^{-1}$; $^1$H NMR (CDCl$_3$, 300 MHz) $\delta$ 6 11.4–10.9 (br s, 1 H), 7.82 (d, J=9.36 Hz, 1 H), 6.40 (d, 9.36 Hz, 1 H), 3.32 (br s, 1 H), 3.02 (dd, J=18.27, 7.11 Hz, 1 H), 2,71 (d, J=18.27 Hz, 1 H), 1.80–1.57 (m, 4 H), 1.66 (d, J=6.75 Hz, 3 H), 1.27–1.13 (m, 2 H), 0.81 (d, J=6.3 Hz, 3 H); $^{13}$C NMR (CDCl$_3$, 75 MHz); $\delta$ 165.0, 144.5 (2C), 139.5, 122.2, 116.8, 111.3, 55.1, 51.2, 42.7, 34.4, 30.6, 26.5, 21.4, 12.3; MS m/e 244 (M+). 2a (axial methyl): IR (neat) 3361, 3276, 3100, 3080, 2949, 2921, 2868, 1659, 1615, 1553, 1457, 834, 735, 615 cm$^{-1}$; $^1$H NMR (CDCl$_3$, 300 MHz) $\delta$ 11.8–11.6 (br s, 1 H), 7.89 (d, J=9.42 Hz, 1 H), 6.44 (d, J=9.45 Hz, 1 H,), 5.50 (q, J=6.75 Hz, 1 H), 3.35-3.31 (m, 1 H), 2.87 (dd, J=17.2, 5.34 Hz, 1 H), 2.64 (d, J=17.1 Hz, 1 H), 1.99-1.93 (m, 1 H), 1.68-1.55 (m, 4 H), 1.67 (d, J=6.69 Hz, 3 H), 1.26-1.16 (m, 2 H), 0.75 (d, J=6.27 Hz, 3 H); $^{13}$C NMR (CDCl$_3$, 75 MHz) δ 165.2, 144.4, 142.6, 140.8, 125.4, 117.5, 112.6, 54.5, 49.7, 37.2, 36.0, 29.7, 27.3, 21.2, 12.2; MS m/e 244 (M+).

EXAMPLE 2

DIHYDRO-DESMETHYL-HUPERZINE

Acrolein (1 ml, 15 mmol) in 10 ml dry methylene chloride was added to a solution containing β-keto ester 18 (2.08 g, 8.85 mmol), 1,1,3,3-tetramethylguanidine (0.2 ml, 1.6 mmol), in 15 ml of dry methylene chloride at −78° C. After the addition, which takes 30 min., the solution was allowed to stir at 78° C. for an additional 1 hr and then allowed to warm to room temperature (−78° C.-25° C., 1 hr), where it was stirred at for an additional 2 hr. Solvent was evaporated and the foamy residue chromatographed on silica gel (1:4, ethyl acetate/hexanes then 1:1, ethyl acetate/hexanes), to give $C_{15}$-desmethyl-19 (2.15 g, 84%) as a 1:1 mixture of isomers.

A solution consisting of $C_{15}$-desmethyl-19 (560 mg, 1.92 mmol), thiocarbonyldiimadazole (456 mg, 2.56 mmol), and 5 ml of THF was heated together in a sealed tube at 65° C. for 20 hr. The solvent was evaporated, and the residue chromatographed on silica gel (2:3, ethyl acetate/hexanes) to give the $C_8$-thiocarbonylimidazole derivative of $C_{15}$-desmethyl-19 (588 mg, 76%) as a white foam consisting of a 1:1 mixture of two isomers. $R_f$ (two isomers)=0.1-0.3 (1:1, ethyl acetate/hexanes); IR (neat); 3131, 2951 br., 2843, 2782, 1729, 1603, 1576, 1480, 1424, 1392, 1329, 1264, 1229, 1096, 1025, 935, 830, 736 cm$^{-1}$.

A solution consisting of the $C_8$-thiocarbonylimidazole derivative (520 mg, 1.30 mmol), n-Bu$_3$SnH (0.785 ml, 1.95 mmol), AIBN (cat.), and 3 ml of toluene was thoroughly purged with argon and then heated at 120° C. for 2.5 hr. The solvent was evaporated and the residue chromatographed on flash silica gel (hexanes then 1:19, ethyl acetate/hexanes) to give $C_{15}$-desmethyl-32 (228 mg, 64%) as a thick oil; IR (neat) 2947, 2870, 1722, 1698, 1575, 1479, 1422, 1265, 1026 cm$^{-1}$.

A solution consisting of (ethyl)triphenylphosphonium bromide (4.13 g, 10.9 mmol) and potassium t-butoxide (1.12 g, 10 mmol) was stirred in 3 ml of THF at 25° C. for 20 minutes. The solution was then cooled to 0° C. and $C_{15}$-Desmethyl-32 (785 mg, 2.8 mmol) in 3 ml of THF was added dropwise. The solution was allowed to warm to 25° C. and stirred for 4 hr. The reaction mixture was quenched with an aqueous ammonium chloride solution and the THF evaporated. The aqueous residue was extracted with ethyl acetate and the combined extracts dried over sodium sulfate. Filtration, evaporation, and column chromatography with silica gel (hexanes then 1:4, ethyl acetates/hexanes) gave $C_{15}$-desmethyl 33 and 34 (685 mg, 84%) as a 2.9/1 mixture of Z/E isomers; IR (mixture, neat); 2940, 2868, 1732, 1577, 1477, 1421, 1314, 1263, 1244, 1026 cm$^{-1}$.

A solution consisting of $C_{15}$-desmethyl 33 and 34 (2.9/1, 684 mg, 2.38 mmol), thiophenol (1.5 ml, 12.7 mmol), and AIBN (500 mg, 3.0 mmol) in 6 ml of toluene was purged with argon and heated at 100° C. for 20 hr. The solvent was evaporated and the residue chromatographed on flash silica gel (hexanes then 1:19, ethyl acetate/hexanes) to give $C_{15}$-desmethyl-33 (595 mg, 87%). None of the Z-isomer is detectable; IR (thin film) 2942, 2866, 1731, 1600, 1577, 1477, 1428, 1328, 1314, 1266, 1245, 1025, 821 cm$^{-1}$. MS m/e 287 (M+), 272, 258; exact mass calculated for $C_{17}H_{21}NO_3$: 287.1521, found: 287.1521.

A solution consisting of $C_{15}$-desmethyl-33 (586 mg, 2.0 mmol), 2 ml 20% aqueous sodium hydroxide solution, 2 ml of THF, and 4 ml methanol were heated together at 70° C. in a sealed tube for a period of 24 hr. The organic solvents were evaporated and the residue brought to a pH of 7 using a 5% aqueous HCl solution. The aqueous solution was then extracted with methylene chloride and the combined extracts dried over sodium sulfate. This was then filtered, evaporated, and chromatographed on a column using silica gel (1:4, ethyl acetate/hexanes) to recover starting materials then 1:1, ethyl acetate/hexanes to give the corresponding carboxylic acid (175 mg, 31%) as a white foam. Yield based on recovered starting material was 56%; IR (neat) 3518-2423 br., 2939, 2868, 2423, 1705, 1599, 1478, 1315, 1265, 1025, 910, 732 cm$^{-1}$.

A solution consisting of $C_{15}$-desmethyl-33-carboxylic acid (165 mg, 0.6 mmol), triethylamine (0.117 ml, 0.9 mmol), and diphenylphosphoryl azide (0.18 ml, 0.8 mmol) in 4 ml toluene was heated at 110° C. for 2 hr. The solvents were evaporated and the residue taken up in 4 ml of dry methanol which was then heated at 70° C. for 1 hr. Evaporation of the methanol followed by column chromatography on silica gel (1:9, ethyl acetate/methylene chloride), yielded the $C_{15}$-desmethyl-33-carbamate (115 mg, 64%) as a white foam; Rf=0.5 (1:9, ethyl acetate/methylene chloride); which was converted into $C_{15}$-desmethyl-($C_8$-$C_{15}$)dihydrohuperzine by treatment with TMSI.

Iodotrimethylsilane (ITMS) (0.94 mL, 6.6 mmol) was added dropwise to a solution consisting of the carbamate (100 mg, 0.33 mmol) in 5 ml of dry chloroform. After the addition, the solution was heated to 65° C. for 10 hr. The chloroform and excess iodotrimethylsilane were evaporated off and the residue taken up in a few ml of methanol, which was then heated at 70° C. for 3 hr. The methanol was evaporated and the residue chromatographed by column-chromatography on silica gel (1:9, methanol/chloroform) which gave product 3 (56.2 mg, 74%) as a white foam; Rf=0.3 (1:9, methanol/chloroform); IR (neat) 3367, 3276, 3121, 2933, 2863, 1658, 1618, 1553, 1460, 911, 832, 731 cm$^{-1}$; $^1$H NMR (CDCl$_3$, 300 MHz) δ 11.3-10.7 (br. s, 1 H), 7.80 (d, J=9.39 Hz, 1 H), 6.39 (d, J=9.36 Hz, 1 H), 5.47 (q, J=6.69 Hz, 1 H), 3.29 br. s, 1 H), 3.02 (dd, J=18.33, 7.17 Hz, 1 H), 2.70 (br d, J=18.30 Hz, 1 H), 1.77-1.46 (m, 7 H), 1.64 (d, J=7.74 Hz, 3 H), 1.37 (d, J=10.1 Hz, 1 H); $^{13}$C NMR (CDCl$_3$, 75 MHz) δ 165.0, 144.8, 144.7, 139.6, 121.5, 116.8, 111.2, 55.1, 42.7, 34.1(2C), 30.5, 20.1, 12.2; MS m/e 230 (M+), 215, 187, 173, 84, 43; exact mass calculated for $C_{14}H_{18}N_2O$: 230.1419, found: 230.1419.

EXAMPLE 3

11-DESMETHYL-11-CHLORO-HUPERZINE A

A. Wittig Reaction of β-Ketoester 20 with Chloromethylenetriphenylphosphorane

To a suspension of 383 mg (1.1 mmol) of (chloromethyl)triphenylphosphonium chloride in 5 ml of dry THF was added dropwise 0.4 ml (1.0 mmol) of n-BuLi (2.5 M in hexane) at 0° C. under argon. The reaction mixture was stirred at room temperature for 15 min, and then cooled to 0° C. The β-ketoester 20 (230 mg, 0.8 mmol) in 2 ml of dry THF was added dropwise to this mixture at 0° C. The resulting mixture was allowed to warm to room temperature and stirred for 1.5 hr. The reaction was quenched with water and the reaction mixture was extracted with ethyl acetate. The ethyl acetate extracts were washed with brine, dried over $Na_2SO_4$, and concentrated by rotary evaporation. The crude product was purified by column chromatography on silica gel with ethyl acetate-hexane (1:12, v/v) and then ethyl acetate-hexane (1:8, v/v) as eluent to give 169 mg (66%) of a mixture of Z-isomer 62 and E-isomer 63 in a ratio of 7:3 by $^1$H-NMR analysis.

The Z-isomer 62 was isolated as colorless prisms: mp 141°–142° C. (hexane-dichloromethane); $R_f$=0.53 ($SiO_2$, 20% ethyl acetate in hexane); IR (thin film) 2943, 1728, 1601, 1580, 1478, 1428, 1321, 1266, 1030, 739 cm$^{-1}$; mass spectrum, m/z 319 and 321 (M$^+$, $^{35}$Cl and $^{37}$Cl), 284 (M$^+$—Cl); exact mass calcd for $C_{17}H_{18}{}^{35}ClNO_3$ 319.0975; found 319.0975. The E-isomer 63 was isolated as a colorless oil: $R_f$=0.56 ($SiO_2$, 20% ethyl acetate in hexane); IR (thin film) 2938, 1734, 1601, 1576, 1478, 1424, 1324, 1248, 1028, 828, 797; mass spectrum m/z 319 and 321 (M$^+$, $^{35}$Cl and $^{37}$), 284 (M$^+$—Cl); exact mass calcd for $C_{17}H_{18}ClNO_3$.

B. Hydrolysis of E-Isomer

The E-isomer 63 (11 mg, 0.04 mmol) was dissolved in 200 μl of THF, and 50 μl of 20% aqueous NaOH was added, followed by 400 μl of MeOH. The mixture was refluxed for 15 hr. THF and MeOH were removed by rotary evaporation, and the aqueous residue was washed with dichloromethane. The aqueous residue was adjusted to a pH of 5 with 5% HCl solution. The solution was extracted with dichloromethane. The dichloromethane extracts were dried over $Na_2SO_4$ and concentrated by rotary evaporation. The crude product was purified by flash column chromatography on silica gel with 10% MeOH in ethyl acetate as eluent to give 11 mg (100%) of the acid 64 as a colorless oil: $R_f$=0.44 ($SiO_2$), ethyl acetate): IR (thin film) 2932, 1694, 1599, 1577, 1476, 1424, 1323, 1269, 1028, 758 cm$^{-1}$; mass spectrum, m/z 305 and 307 (M$^+$, $^{35}$Cl and $^{37}$Cl), 270 (M$^+$—Cl); exact mass calcd for $C_{16}H_{16}ClNO_3$.

C. Preparation of Carbamate 65

To a solution of the acid 64 (40 mg, 0.13 mmol) in 3 ml of dry toluene was added 19 μl (0.14 mmol) of $NEt_3$ and 29 μl (0.13 mmol) of diphenylphosphoryl azide. The mixture was refluxed under argon for 1 hr. After cooling, 3 ml of dry MeOH was added and the mixture was refluxed for an additional 2.5 hr under argon. Toluene and MeOH were removed by rotary evaporation. The crude product was purified by flash column chromatography on silica gel with dichloromethane-ethyl acetate (9:1, v/v) as eluent to give 33 mg (76%) of the carbamate 65 as colorless prisms: mp 161–163° C. (ethyl acetate); $R_f$=0.52 ($SiO_2$, 40% ethyl acetate in hexane); IR (thin film) 3312, 2936, 1709, 1597, 1476, 1323, 1260, 1032, 760 cm$^{-1}$; mass spectrum, m/z 334 and 356 (M$^+$, $^{35}$Cl and $^{37}$Cl), 299 (M$^+$—Cl); exact mass calcd for $C_{17}H_{19}ClN_2O_3$.

D. Preparation of Cl-Derivative 13

To a solution of the carbamate 65 (35 mg, 0.10 mmol) in 4 ml of dry chloroform was added 150 ul (1.05 mmol) of $Me_3SiI$ under argon at room temperature, and the resulting mixture was refluxed for 16 hr under argon. MeOH (4 ml) was added, and the solution was refluxed for an additional 7 hr. The solvent was removed by rotary evaporation. The crude product was purified by flash column chromatography on silica gel with chloroform-MeOH—$NH_4OH$ (46:5:0.5, v/v) as eluent to give 23 mg (85%) of the Cl-derivative 13 as colorless prisms: mp 238–240° C. (dec.) (acetone); $R_f$=0.23 ($SiO_2$, chloroform-MeOH=9:1, v/v); IR (KBr) 3385, 2963, 1661, 1616, 1554, 1466, 1424, 1308, 816 785 cm$^{-1}$; mass spectrum, m/z 262 and 264 (M$^+$, $^{35}$Cl and $^{37}$Cl), 227 (M$^+$—Cl); exact mass calcd for $C_{14}H_{15}ClN_2O$.

EXAMPLE 4

DETERMINATION OF ACHE ACTIVITY

Rats were killed by decapitation and the brains were extirpated rapidly. The hippocampus was dissected out on ice according to the method of J. Glowinski et al., *Neurochem.*, 13, 655 (1966). Samples were homogenized in ice-cold 0.32 M sucrose. Homogenates were centrifuged at 1000×g for 10 min to remove cell nuclei and heavy debris. The supernatant was then aspirated off and spun again (12000×g) for 20 min to form a pellet (Whittaker's $P_2$ fraction) that contained synaptosomes and mitochondria (V. P. Whittaker et al., *Prog. Biophys. Mol. Biol.*, 15, 39 (1965)). The pellet was resuspended in 0.32 M sucrose. A portion of this synaptosome-rich fraction was added in triplicate to ice-cold pH 7.4 Krebs-Ringer medium.

Assay of AChE was carried out according to the method described in C. R. Mantione et al., *J. Neurochem.*, 41, 251 (1983). Tissue homogenate was incubated for 30 min at 30° C. in a final volume of 20 μl containing 75 mM sodium phosphate buffer, pH 7.0, and 1.5 mM [$^{14}$C]acetylcholine (1.9 mCi/mmol). To each sample was added 25 μl of cold water, followed by 150 μl of tetraphenylboron solution (F. Fonnum et al., *Biochem. J.*, 115, 465 (1975)). The tubes were vortexed for 10 sec, then centrifuged for 1 min. The bottom aqueous layer was quickly frozen in a dry ice/acetone bath, and the top organic layer aspirated off. Finally, the buffer was allowed to thaw, and a 25 μl portion was counted for the amount of [$^{14}$C]acetate formed. The amount of residual [$^{14}$C]acetylcholine left in the buffer by the extraction step alone was determined by subtracting from the tissue sample values of [$^{14}$C]acetylcholine measured in a blank sample that contained buffer and substrate, but no tissue.

All of the patent documents and publications cited above are incorporated by reference herein, as though fully set forth.

The invention has been described with reference to various specific and preferred embodiments and techniques. However, it should be understood that many variations and modifications may be made while remaining within the spirit and scope of the invention.

What is claimed is:

1. A compound of the formula (I):

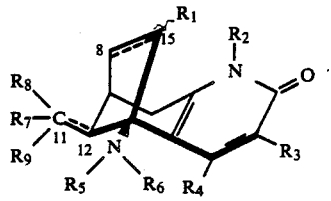

wherein $R_1$ is H $(C_1-C_8)$alkyl or halo; $R_2$ is H or $(C_1-C_8)$alkyl; $R_3$ and $R_4$ are individually H, $(C_1-C_8)$alkyl, $NO_2$, hydroxy or halo; $R_5$ and $R_6$ are individually H, $(C_1-C_8)$alkyl, aryl or aralkyl; $R_7$ is H, halo or $(C_1-C_8)$alkyl, $R_8$ is halo or $(C_1-C_8)$alkyl, $R_9$ is absent or is H; and the bonds represented by—are individually absent or, together with the adjacent bond, form the unit C≡C, with the proviso that if both of the bonds represented by—are present, $R_3$ and $R_4$ cannot both be H unless $R_7$ or $R_8$ is halo; and the pharmaceutically acceptable salts thereof.

2. The compound of claim 1 wherein the $C_8-C_{15}$ bond is absent.

3. The compound of claim 2 wherein $R_1$ is $(C_1-C_8)$alkyl.

4. The compound of claim 3 wherein $R_1$ is equatorial $(C_1-C_8)$alkyl.

5. The compound of claim 3 wherein $R_1$ is axial $(C_1-C_8)$-alkyl.

6. The compound of claims 4 or 5 wherein $R_1$ is methyl.

7. The compound of claim 1 wherein $R_1$ is fluoro.

8. The compound of claim 1 wherein $R_1$ is H.

9. The compound of claim 1 wherein the $C_{11}-C_{12}$ bond is absent.

10. The compound of claim 9 wherein $R_7$ is H, $R_9$ is H and $R_8$ is $(C_1-C_8)$alkyl.

11. The compound of claim 10 wherein the $C_{11}-C_{12}$ bond is axial.

12. The compound of claim 10 wherein the $C_{11}-C_{12}$ bond is equatorial.

13. The compound of claim 1 wherein $R_3$ is $(C_1-C_4)$alkyl, $NO_2$, hydroxy or halo.

14. The compound of claim 1 wherein $R_4$ is $(C_1-C_4)$alkyl, $NO_2$, hydroxy or halo.

15. The compound of claims 13 or 14 wherein $R_4$ is chloro or methyl.

16. The compound of claim 1 wherein the $C_8-C_{15}$ bond is present, the $C_{11}-C_{12}$ bond is present and $R_8$ is halo.

17. The compound of claim 16 wherein $R_8$ is chloro.

18. A pharmaceutical composition comprising a therapeutically effective amount for the inhibition of the cholinesterase enzymes in a mammal of one or more compounds of claim 1 and a pharmaceutically acceptable carrier.

19. A therapeutic method comprising inhibiting the cholinesterase enzymes in a mammal by administering to said mammal an effective amount of one or more of the compounds of claim 1.

* * * * *